(12) United States Patent
Huth et al.

(10) Patent No.: US 7,955,623 B2
(45) Date of Patent: Jun. 7, 2011

(54) PHARMACEUTICAL PREPARATIONS FOR TREATING INFLAMMATORY DISEASES

(75) Inventors: Karin Christine Huth, Munich (DE); Korbinian Brand, Hannover (DE)

(73) Assignee: Karin Huth, Munich (DE)

( * ) Notice: Subject to any disclaimer, the term of this patent is extended or adjusted under 35 U.S.C. 154(b) by 393 days.

(21) Appl. No.: 12/148,724

(22) Filed: Apr. 22, 2008

(65) Prior Publication Data
US 2009/0263498 A1 Oct. 22, 2009

(51) Int. Cl.
*A61K 33/40* (2006.01)
*A61K 8/00* (2006.01)
*A61Q 11/00* (2006.01)
*A01N 39/00* (2006.01)
*A01N 25/00* (2006.01)

(52) U.S. Cl. .......... 424/613; 424/49; 424/405; 514/885; 514/886; 514/887

(58) Field of Classification Search .................. None
See application file for complete search history.

(56) References Cited

U.S. PATENT DOCUMENTS

| | | | |
|---|---|---|---|
| 6,258,384 B1 * | 7/2001 | Stanley et al. | 424/600 |
| 7,172,426 B1 * | 2/2007 | Lynch et al. | 433/224 |
| 2003/0211465 A1 | 11/2003 | Mundschenk et al. | |
| 2004/0220264 A1 * | 11/2004 | Yu et al. | 514/554 |

OTHER PUBLICATIONS

Huth et al. (J Dent Res May 2007, 86(5), 451-456).*
Kotiaho et al. (J Am Soc Mass Spectrom 2000, 11, 526-535).*
Mudd et al. (Atmospheric Environment 1969, 3(6), 669-682).*
Read, New Scientist, 1989; p. 40; 1 page.*
Grinwald, Chemokine Research Trends, 2007, Nova Publishers; p. 12; 1 page.*
Ghosh, Handbook of transcription factor NF-kappaB, 2007, CRC Press; pp. 195-196; 3 pages.*
Arita, M., et al., Microbicidal efficacy of ozonated water against *Candida albicans* adhering to acrylic denture plates. *Oral Microbiology and Immunology*. vol. 20 pp. 206-210 (2005).
Bartold, P.M., and Narayanan, A.S., Molecular and cell biology of healthy and diseased periodontal tissues. *Periodontology*. vol. 40 pp. 29-49 (2006).
Baysan, A., and Lynch, E., Effect of ozone on the oral microbiota and clinical severity of primary root caries. *American Journal of Dentistry*. vol. 17, No. 1. pp. 56-60 (2004).
Bonizzi, G., and Karin, M., The two NF-$\kappa\beta$ activation pathways and their role in innate and adaptive immunity. *Trends in Immunology*. vol. 25, No. 6 pp. 280-288 (2004).
Capello, C., et al., Ozonized Low Density Lipoprotein (ozLDL) Inhibits NF-$\kappa\beta$ and IRAK-1-Associated Signaling. *Arteriosclerosis, Thrombosis and Vascular Biology*, pp. 226-232 (2007).
Cataldo, Franco, On the action of ozone on proteins. *Polymer Degradation and Stability*. vol. 82 pp. 105-114 (2003).
Chen, G., and Goeddel, D.V., TNF-R1 Signaling: A Beautiful Pathway. *Science*. vol. 296 pp. 1634-1635 (2002).

Ebensberger, U., et al., PCNA-expression of cementoblasts and fibroblasts on the root surface after extraoral rinsing for decontamination. *Dental Traumatology*. vol. 18 pp. 262-266 (2002).
Filippi, A., The effects of ozonized water on epithelial wound healing. *Deutsche Zahnärztliche Zeitschrift*. vol. 56 pp. 104-108 (2001).
Gamonal, J., et al., Levels of Interleukin-1$\beta$, -8, and -10 and RANTES in Gingival Crevicular Fluid and Cell Populations in Adult Periodontitis Patients and the Effect of Periodontal Treatment. *Journal of Periodontology*. vol. 71, No. 10 pp. 1535-1545 (2000).
Graves, D. T., et al., Periodontal disease: bacterial virulence factors, host response and imact on systemic health. *Current Opinion in Infectious Diseases*. vol. 13 pp. 227-232 (2000).
Haddad, E.-B., et al., Ozone induction of cytokine-induced neutrophil chemoattractant (CINC) and nuclear factor-$\kappa$b in rat lung: inhibition by corticosteroids. *FEBS Letters*. vol. 379 pp. 265-268 (1996).
Honda, T., et al., Balance of inflammatory response in stable gingivitis and progressive periodontitis lesions. *Clinical and Experimental Immunology*. vol. 144 pp. 35-40 (2006).
Huth, K.C., et al., Effect of ozone on oral cells compared with established antimicrobials. *European Journal of Oral Sciences*. vol. 114 pp. 435-440 (2006).
Laskin, D.L., et al., Upregulation of phosphoinositide 3-kinase and protein kinase B in alveolar macrophages following ozone inhalation. Role of NF-$\kappa\beta$ and STAT-1 in ozone-induced nitric oxide production and toxicity. *Molecular and Cellular Biochemistry*. vol. 234-235 pp. 91-98 (2002).
Lin, C., et al., Effects of Root-End Filling Materials and Eugenol on Mitochondrial Dehydrogenase Activity and Cytotoxicity to Human Periodontal Ligament Fibroblasts. *Journal of Biomedical Materials Research Part B Applied Biomaterials*. vol. 71B pp. 429-440 (2004).
Madianos, P.N., et al., Generation of inflammatory stimuli: how bacteria set up inflammatory responses in the gingiva. *Journal of Clinical Periodontology*. vol. 32 pp. 57-71 (2005).
Márton, I.J., and Kiss, C., Protective and destructive immune reactions in apical periodontitis. *Oral Microbiology and Immunology*. vol. 15 pp. 139-150 (2000).
Nagayoshi, M., et al., Antimicrobial Effect of Ozonated Water on Bacteria Invading Dentinal Tubules. *Journal of Endodontics*. vol. 30, No. 11 pp. 778-781 (2004).
Nagayoshi, M., et al., Efficacy of ozone on survival and permeability of oral microorganisms. *Oral Microbiology and Immunology*. vol. 19 pp. 240-246 (2004).
Nair, P.N.R. Pathogenesis of Apical Periodontitis and the Causes of Endodontic Failures. *Critical Reviews in Oral Biology and Medicine*. vol. 15, No. 6 pp. 348-381 (2004).
Nichols, T.C., et al., Role of Nuclear Factor-Kappa B (NF-$\kappa\beta$) in Inflammation, Periodontitis, and Atherogenesis. *Annals of Periodontology*. vol. 6, No. 1 pp. 20-29 (2001).

(Continued)

*Primary Examiner* — Ernst V Arnold
(74) *Attorney, Agent, or Firm* — Jenkins, Wilson, Taylor & Hunt, P.A.

(57) ABSTRACT

The present invention refers to a pharmaceutical preparation for treating inflammatory diseases and microbial infections comprising a pharmaceutically effective amount of ozone and at least one monomeric amino acid having an oxidation-sensitive side chain, or at least one ozonized monomeric amino acid having an oxidation-sensitive side chain.
Also described is the use of a preparation as described before for providing a medicament for treating inflammatory diseases, microbial infections and for immune modulation. The pharmaceutical preparation according to the invention is particularly useful in the treatment of oral inflammations.

17 Claims, 4 Drawing Sheets

OTHER PUBLICATIONS

Page, S., et al., 4-Hydroxynonenal Prevents NF-κβ Activation and Tumor Necrosis Factor Expression by Inhibiting IκB Phosphorylation and Subsequent Proteolysis. *The Journal of Biological Chemistry.* vol. 274, No. 17 pp. 11611-11618 (1999).

Paraskeva, P., and Graham, N.J.D., Ozonation of Municipal Wastewater Effluents. *Water Environment Research.* vol. 74, No. 6. pp. 569-581 (2002).

Restaino, L., et al., Efficacy of Ozonated Water against Various Food-Related Microorganisms. *Applied and Environmental Microbiology.* vol. 61, No. 9 pp. 3471-3475 (1995).

Sabeti, M., et al., Detection of Receptor Activator of NF-κβ Ligand in Apical Periodontitis. *Journal of Endodontics.* vol. 31, No. 1 pp. 17-18 (2005).

* cited by examiner

PHARMACEUTICAL PREPARATIONS FOR TREATING INFLAMMATORY DISEASES

FIELD OF THE INVENTION

The present invention refers to a pharmaceutical preparation, particularly for treating and preventing inflammatory diseases and microbial infections as well as therapeutical uses of this preparation.

BACKGROUND OF THE INVENTION

Currently, ozone is being discussed in dentistry as a possible alternative oral antiseptic agent. Its high antimicrobial power, also against oral pathogens, without resistance development has been reported not only for gaseous ozone (Paraskeva and Graham, 2002; Baysan and Lynch, 2004) but also for ozone in aqueous solution (Restaino et al., 1995; Nagayoshi et al., 2004a,b; Arita et al., 2005). Ozone gas has been found to significantly decrease the viability of oral cells in the currently used concentrations in dentistry. In comparison, aqueous ozone revealed a high level of biocompatibility to fibroblasts, cementoblasts and epithelial cells (Filippi, 2001; Ebensberger et al., 2002; Nagayoshi et al., 2004b), which suggests its use against oral infectious diseases where it comes into contact with resident oral cells, e.g. marginal and apical periodontitis.

Marginal and apical periodontitis result not from pathogenic bacteria alone but from the interaction of pathogens and host immune response mechanisms (Honda et al., 2006; Nair, 2004). Therefore, the immune-modulatory effect of treatment strategies proposed for these diseases must also be considered. Both disease entities are characterized by an inflammatory reaction involving different oral hard- and soft-tissue compartments, e.g. the marginal gingiva, periodontal attachment fibers or the alveolar bone (Bartold and Narayanan, 2006; Nair, 2004). The inflammatory process is primarily induced by pathogen-associated molecular patterns, particularly by bacterial lipopolysaccharides (Madianos et al., 2005). The subsequent activation of the inflammatory molecular cascade leads to the expression of several proinflammatory cytokines, e.g. interleukin-1, interleukin-8 and tumor necrosis factor (TNF) that ultimately mediate the destruction of the alveolar bone and periodontal connective tissue (Márton and Kiss, 2000; Graves et al., 2000; Gamonal et al., 2000).

The transcription factor NF-κB plays a pivotal role in the regulation of inflammatory/immune processes and apoptosis (Bonizzi and Karin, 2004). Also for the regulation of periodontal/periapical inflammatory reactions and the pathogenesis of periodontitis, the functional activity of NF-κB has been suggested to be of paramount significance (Nichols T C et al., 2001; Sabeti et al., 2005; Bartold and Narayanan, 2006). NF-κB exists as a dimer which is trapped in the cytosol by inhibitory proteins, e.g. IκBA (Bonizzi and Karin, 2004). The NF-κB-system is activated by numerous agents including cytokines (e.g. TNF, interleukin-1) and microbial pathogens/products. The activation of NF-κB is mediated by the IκB kinase complex that phosphorylates IκB which is subsequently degraded by the proteasome. The thus freed NF-κB translocates to the nucleus where it binds to κB sequences in promoters/enhancers thereby regulating the expression of various genes such as interleukin-1/-8 or TNF.

In the publication "Ozonized low density lipoprotein (ozLDL) inhibits NF-κB . . . ", Cappello et al. disclose the characteristics of LDL exposed to ozone. However, this citation does not disclose monomeric amino acids which have been ozonized. The agent, which is able to inhibit NF-κB-activation is described as being ozonized cholesterol. Furthermore, it is not disclosed that the proteins are being cleaved by ozonisation and, thus, this publication does not disclose monomeric amino acids as indicated above. Furthermore, this publication is silent on a potential anti-inflammatory effect of ozonized amino acids.

US 2003/211465 discloses ozonized polypeptides, however, not monomeric single amino acids. This publication is related to the prevention of HIV (i.e. is related to viral diseases). Again, also this publication is silent on anti-inflammatory effects of the ozonized amino acids.

Huth et al. "Effect of ozone on oral cells compared with established antimicrobials" describes the antimicrobial effect of ozonized water. However, again, ozonized monomeric amino acids are not disclosed and, furthermore, it is not disclosed that they have an anti-inflammatory effect.

Ozone gas is known to activate NF-κB under certain conditions (Haddad et al., 1996; Laskin et al., 2002). However, it is not known if aqueous ozone also interferes with the NF-κB-system. This is important, as an activation of NF-κB might adversely affect the therapeutic benefit of aqueous ozone when used e.g. against marginal and apical periodontitis.

BRIEF DESCRIPTION OF THE INVENTION

One problem of the present invention was to investigate the effect of aqueous ozone on NF-κB-associated signaling/transcription in oral cells and its implication on medical therapy. It is a further problem of the present invention to provide a pharmaceutical preparation effective in the treatment or prophylaxis, particularly of inflammatory diseases and microbial infections, especially in the oral, dental or throat region, in order to overcome the problems associated with prior art treatment methods for those diseases. Additionally, there is a need for improving anti-inflammatory and antimicrobial agents which have been used up to now in the state of the art, particularly in dental medicine.

These problems are achieved by a pharmaceutical preparation which is characterized by what is stated in the independent claim. The preferred embodiments of the invention are disclosed in the dependent claims. Further advantages and embodiments comprised by the present invention are included in the present description as well as in the examples.

DETAILED DESCRIPTION OF THE INVENTION

The inventors have surprisingly found that a pharmaceutical preparation comprising—each in a pharmaceutically effective amount—ozone and at least one monomeric amino acid having one or more oxidation-sensitive side chains, or at least one amino acid which has been previously treated with ozone can be effectively used for treating and preventing inflammatory diseases. It can also be used for immune-modulation purposes.

The present inventors have elucidated that monomeric amino acids having an oxidation-sensitive side chain after having been treated with ozone, or ozonized amino acids, could efficiently alleviate or even cure inflammatory diseases and microbial infections. Cell culture experiments were made wherein human oral epithelial cells and fibroblasts as well as HeLa-cells were treated with the pro-inflammatory cytokine TNF-α in order to activate the NF-κB system. Preincubating such treated cells with ozone in aqueous solution did show no effect. However, when adding those monomeric amino acids to the aqueous solution to be ozonized, an efficient and dosage dependent inhibition of the NF-κB system without any toxic effect could be shown. This could also be shown when pre-incubating the cells with resolved lyophilized ozonized amino acids, implicating that the effect is not dependent on the presence of ozone in the solution next to the ozonized amino acid. Hence the inventors could prove for the first time that ozonized amino acids or amino acids in the presence of ozone or ozonized amino acids alone could be used efficiently as a therapeutic agent not showing the disadvantages of prior art medicaments like antiseptics such as chlorhexidin digluconate.

In one embodiment of the invention, the at least one monomeric amino acid having an oxidation-sensitive side chain is used in aqueous solution which has been treated with ozone. In a further embodiment, the at least one monomeric amino acid having an oxidation-sensitive side chain is pre-treated with ozone, e.g. in aqueous solution, to obtain an ozonized amino acid, lyophilised and the lyophilised substance can then be used either in dry form or in dissolved form in a pharmaceutical preparation. The dry lyophilised ozonized amino acid can be resolved either in aqueous or non-aqueous solutions, e.g. polar solvents such as alcohols or acetone. Depending on the chemical nature of the pharmaceutical preparation in combination with the mode of administration to be used, the pharmaceutical preparation is either in fluid form or in solid form, e.g. in powder form.

In one embodiment of the present invention monomeric amino acids having an oxidation-sensitive side chain dissolved in an aqueous solution. The aqueous solution is treated with ozone. This is preferably done by using an ozone generator as commercially available by different suppliers. The amount of ozone to be added can be varied in accordance with the patients' needs and the therapeutical potential to be achieved and can be determined by laboratory experiments starting with low ozone concentrations to higher ozone concentrations and determining the effectiveness with respect to e.g. the inhibitory effect on inflammation associated signaling/transduction and microorganisms. Preferably, an amount of 0.01-20 µg/ml ozone in aqueous solution is used. This was achieved by treating the aqueous solution with ozone gas, e.g. with 75 µg/ml for 15 min and then dissolving the solution further. Even lower or higher amounts can be used. The preferred ranges, however, lie within the limits of 0.01-20 µg/ml ozone in aqueous solution.

The effective amount of amino acids can also be determined by ordinary laboratory experiments. Generally, the amount of amino acids will be dependent on the amount of ozone for ozonation and vice versa. In a preferred embodiment, the amino acids are present in an amount of 0.01-100 g/l while even lower or higher amounts, e.g. 0.001-400 g/1 may be used. However, the preferred ranges lie within 0.01-100 g/l.

In a further preferred embodiment, the amino acids or amino acids containing compounds are pre-treated with ozone in order to obtain ozonized monomeric amino acids having an oxidation-sensitive side chain. These pre-treated amino acids are then used in aqueous or any other solution in the pharmaceutical preparation. The amount of ozonized amino acids to be used is similar to the amount described above for the non-pretreated monomeric amino acid having an oxidation-sensitive side chain, i.e. those amino acids not ozonized before use.

While we do not want to be bound to a particular explanation, it seems that the ozone treatment of the monomeric amino acids having an oxidation-sensitive side chain causes oxidation of the amino acids. The oxidation-sensitive side chains of the amino acids react with the ozone, which is reduced by this way. This reaction will occur best for oxidation-sensitive amino acids such as cysteine, methionine, tryptophan, tyrosine, phenylalanine, histidine, arginine belonging to the group of sulfur containing amino acids, aromatic amino acids, and/or amino acids having at least one unsaturated functional group. The amino acids having an oxidation-sensitive side chain (oxidation-sensitive amino acids) could also be regarded as those amino acids which are rich in electrons.

The term "oxidation" as used herein means the loss of electrons by a molecule and an increase of the oxidation number of one or more of its atoms.

These ozonized amino acids show an unexpected and improved anti-inflammatory effect and inhibition of the NF-κB-system as it is derivable from FIG. 3.

Generally, all kind of monomeric amino acids having an oxidation-sensitive side chain can be used according to the present invention. In order to determine their effectiveness, a person skilled in the art is able to perform ordinary experiments to ascertain the most useful and powerful amino acids. Generally, the amino acids are selected from sulfur containing amino acids, aromatic amino acids, and/or amino acids having at least one unsaturated functional group. Those may comprise basic amino acids, acidic amino acids, polar amino acids, non-polar amino acids or a combination thereof. Preferred sulfur containing amino acids are cysteine and methionine, a preferred aromatic amino acid is tryptophan, a preferred basic amino acid arginine and a preferred non-polar amino acid alanine. Further preferred amino acids are phenylalanine, tyrosine, histidine. Particularly preferred are the amino acids cysteine, tryptophan and methionine.

Summarizing, it will be within the knowledge of a person skilled in the art to determine the optimum effective concentration of ozone and amino acid of ozonized amino acid, as well as the chemical nature of the particular amino acid to be used by laboratory experiments by comparing different concentrations of the compounds as well as different compounds themselves with each other, wherein the concentrations, the amino acids and their combinations are varied for finding out the optimum conditions. As a guideline, the preferred embodiments described herein can be used by the skilled artisan.

The present pharmaceutical preparation can be used in the form of formulations generally known by a pharmaceutical engineer and physician. For ease-of-reference, we refer to the U.S. Pharmacopeia, latest edition. Particularly preferred are solid and liquid pharmaceutical compositions comprising pharmacentically active amounts of the ozone and the amino acids or the ozonized amino acids. Further preferred formulations are injectable formulations, creams, lotions for topical application, aerosols, powders, granulates, tablets or capsules. The pharmaceutical compositions are preferably sterile, non-pyrogenic, and isotonic.

The pharmaceutical preparation of the present invention may also contain excipients like stabilizers, surfactants, salts and/or buffering agents. Further excipients may be colorants, sweateners, detergents, preserving agents and pH adjusting agents. Additionally, odor additives, emulsifiers, anti-degradants, consolidating substances, materials and substances for controlled-release delivery can be included.

In a further preferred embodiment, the presently described pharmaceutical preparations contain further pharmaceutically active substances. Examples are: antimicrobial agents such as an ozonized aqueous solution, chlorhexidin digluconate, alcohols, sodium hypochlorite, fluorides etc., antibiotic agents, additional anti-inflammatory substances, analgetics, anaesthetics, soothing herbal essences or oils, buffers, blood circulation enhancing substances, ozonized lipoproteins, ozonized oils, ozonized phospholipids, ozonized cholesterol and ozonation products of cholesterol and ozonation products of phospholipids.

The pharmaceutical preparation of the present invention is particularly useful for the treatment of inflammatory diseases, microbial infections and for immune-modulation. Generally, all kind of inflammatory diseases occurring in humans and animals may be treated. Examples are dermal and mucosal inflammatory diseases, viral, bacterial or fungal caused diseases as well as wound-healing disturbances or ulcera.

In a particularly preferred embodiment, the pharmaceutical preparations of the present invention is used for treating oral inflammations. Examples for these oral inflammations are periodontal disease and apical periodontitis including infected endodontic root canals, gingivitis, impaired wound healing or after surgical interventions as well as periimplantitis or caries and gingivitis preventive or treating mouthrinse and in order to rinse one or more periodontal pocket(s).

The composition of the invention can also be used in the prophylactic treatment of those diseases described above.

The preparation preferably is administered in a single dosage volume of 5-10 ml and the treatment is performed for about 1 min at least once. Other dosage regimens can be used instead, depending on the intended application and the condition or disease to be treated. Thus, the administration can be performed once, twice three times or more per day and the dosage volume may exceed 10 ml or may be lower than 5 ml (for example in pediatric applications). The same is true for the time period of the treatment, which might be longer or shorter depending on the circumstances of the individual case.

While being not bound to a particular interpretation of the mode of action of the present pharmaceutical preparation, it is believed that the ozonized amino acids in aqueous or any other solution or as solid substrate inhibit the NF-κB system and thereby could exert an anti-inflammatory and immune modulatory capacity. In particular, the additional ozone within the solution provides the antimicrobial capacity.

The invention will now be further illustrated by the following non-limiting examples and the figures.

Figure 1:
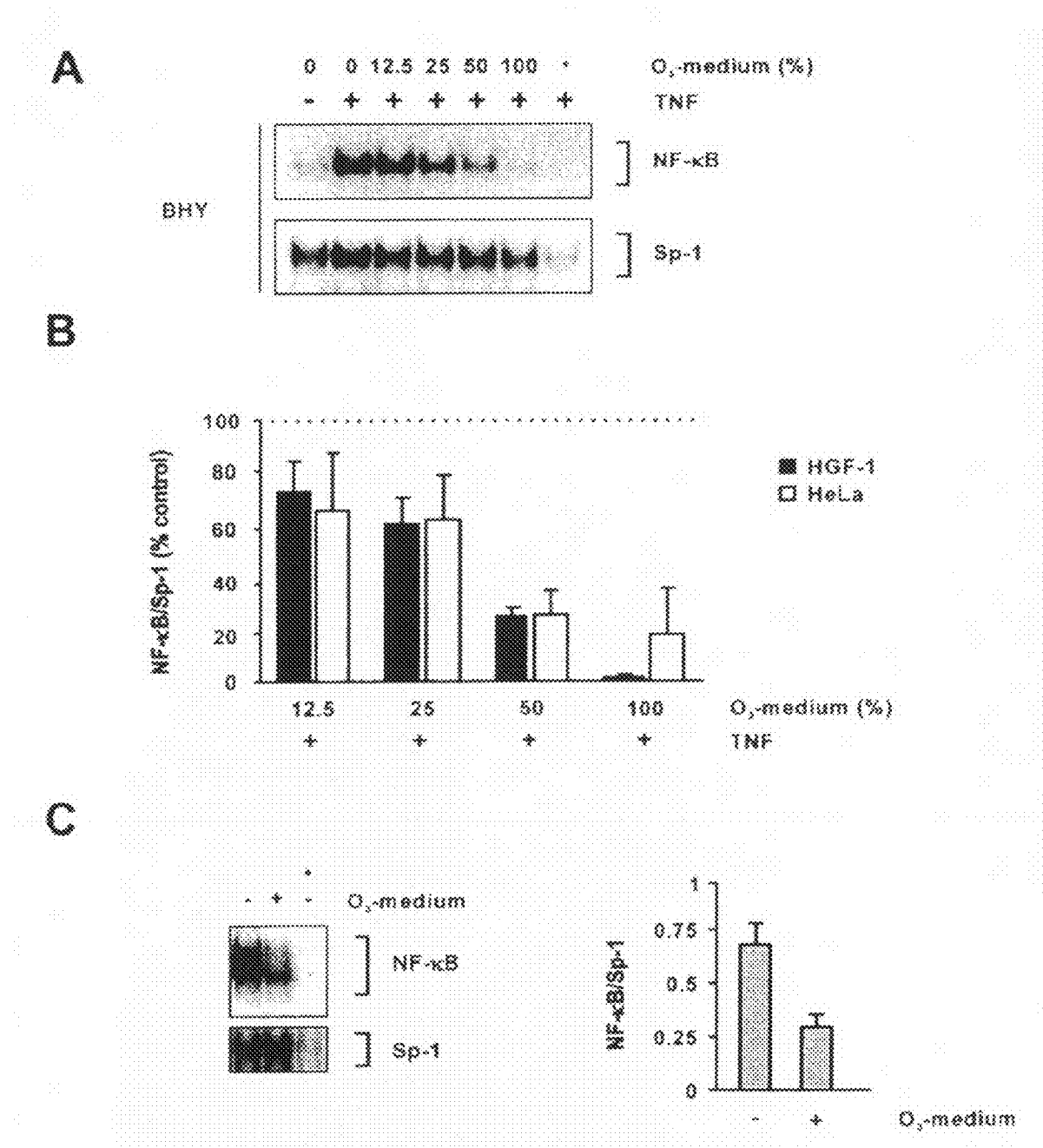
FIG. 1

Activation of NF-κB is inhibited in the presence of $O_3$-medium. A) BHY cells were preincubated with serum-free $O_3$-medium (15 min; the ozonation state is indicated in %) before TNF was added (20 ng/mL, 45 min) and electrophoretic mobility shift assay was performed (NF-κB and Sp-1 binding). The asterisk marks a control reaction in which a 100-fold concentration of unlabeled consensus oligonucleotide was added. B) Cells were treated with $O_3$-medium (HGF-1, 45 min; HeLa, 1 hr) followed by stimulation with TNF (HGF-1, 5 ng/mL for 45 min; HeLa, 1 ng/mL for 15 min). NF-κB-activity normalized to Sp-1 is shown (densitometric analysis). NF-κB-activity after TNF stimulation following preincubation with non-ozonized medium was defined as 100% (dashed line) (n=3, mean±SD). C) Periodontal ligament tissue debris separated into equal-sized portions was incubated (1 hr, 37° C.) with serum-free non-ozonized medium (indicated by "−") or $O_3$-medium (100% ozonation state, indicated by "+") followed by 2 hr incubation in fresh medium without ozone. The samples were shock frozen, homogenized and nuclear extracts prepared. Left: Electrophoretic mobility shift assays were performed (NF-κB and Sp-1 binding). The asterisk marks a control reaction in which a 100-fold concentration of unlabeled consensus oligonucleotide was added. Right: Densitometrically measured NF-κB-activity was normalized to Sp-1 (n=3, mean±SD).

FIG. 2

Effect of $O_3$-medium on IκBα proteolysis, NF-κB-dependent gene expression and κB-dependent transcription. A) IκBA proteolysis is prevented in $O_3$-medium-cultivated cells. BHY (left panel) and HeLa cells (right panel) were preincubated with serum-free $O_3$-medium (BHY, 15 min; HeLa, 1 hr) (ozonation state in %) before TNF was added (BHY, 20 ng/mL, 45 min; HeLa, 1 ng/mL, 15 min). IκBα and actin were determined by Western blot analysis. B) and C) NF-κB target gene expression is inhibited by preincubation with $O_3$-medium. B) BHY and HGF-1 cells were preincubated with serum-free $O_3$-medium (BHY, 15 min; HGF-1, 45 min) followed by TNF (BHY, 20 ng/mL, 45 min; HGF-1, 5 ng/mL, 45 min). Then, the supernatant was replaced by regular medium and interleukin-8 was measured after 5 hr using an enzyme-linked immunosorbent assay (BHY, n=2; HGF-1, n=3; mean±SD). C) BHY cells were pretreated with $O_3$-medium (15 min). The supernatant was replaced by regular medium, TNF (20 ng/mL, 45 min) was added, and interleukin-1β was measured after 12 hr (immunoassay). The interleukin-1β level after TNF-stimulation following pre-treatment with non-ozonized medium was defined as 100% (dashed line) (n=3, mean±SD). D) κB-dependent transcription is inhibited by preincubation with $O_3$-medium. HeLa cells were transfected with pGL2-3κB-Luc and the Renilla plasmid. After 24 hr, cells were treated with serum-free $O_3$-medium (1 hr) followed by TNF (1 ng/mL, 15 min). The supernatant was replaced by regular medium and relative luciferase-activity was measured after 5 hr (n=3, mean±SD).

FIG. 3

$O_3$-amino acids selectively inhibit the NF-κB-system. A) HeLa cells were incubated with $O_3$-phosphate-buffered saline (1 hr) followed by TNF stimulation (1 ng/mL, 15 min). The ozonation state is indicated in %. Electrophoretic mobility shift assay was performed to determine NF-κB-activity as well as Sp-1 binding. B) Cells were preincubated (1 hr) with non-ozonized or ozonized amino acids (medium concentration) dissolved in phosphate-buffered saline (100% ozonation state) followed by stimulation with TNF (1 ng/mL, 15 min). The activation of NF-κB was determined by electrophoretic mobility shift assay. C) Densitometric analysis of the NF-κB-activity normalized to Sp-1 is shown (n=3, mean±SD). NF-κB-activity of cells preincubated with non-ozonized amino acids in phosphate-buffered saline and stimulated with TNF was defined as 100% (dashed line). D) HeLa cells were preincubated with non-ozonized or ozonized glucose (medium concentration) followed by TNF stimulation. The NF-κB-activity compared to Sp-1 binding was determined by electrophoretic mobility shift assay.

FIG. 4

Inhibition of NF-κB by aqueous ozone. In this study preincubation with aqueous ozone ($O_3$-medium) leads in TNF-stimulated cells to an inhibition of IκBα proteolysis (Western blot analysis), NF-κB DNA binding (electrophoretic mobility shift assay), and κB-dependent transcription (luciferase assay) as well as reduced expression of the target genes interleukin-8 and -1β (immunoassay). This indicates that aqueous ozone inhibits NF-κB signaling at the level and/or upstream of IκBα. In the figure the classical NF-κB dimer is depicted which consists of the subunits p65 and p50. The activation pathway of NF-κB is described in more detail in the Introduction.

MATERIALS & METHODS

Culture Conditions

Human oral epithelial cells (BHY, ACC404, DSMZ, Braunschweig, Germany), gingival fibroblasts (HGF-1, ATCC-CRL-2014, LGC-Promochem, Teddington, UK) and HeLa cells (DSMZ) were cultured under standard conditions:

BHY and HGF-1 in DMEM (PromoCell, Heidelberg, Germany) and HeLa in RPMI-1640 medium (Biochrom, Berlin, Germany) (7% or 10% fetal calf serum, respectively), both containing 100 U/mL penicillin and 100 µg/mL streptomycin (Biochrom). The proteasome inhibitor PSI was from Calbiochem (Darmstadt, Germany). A potential toxicity of culture conditions was monitored by cell morphology/count, trypan-blue-exclusion and the Luminescent-Cell-Viability-Assay (Promega, Mannheim, Germany). Furthermore, we gained periodontal ligament tissue debris adherent to the middle third of the root surface of permanent teeth (Lin et al., 2004) following extraction due to peridontitis-associated destruction with patients' informed written consent. Hematoxylin-eosin-staining revealed the predominance of fibroblasts in this tissue (data not shown). Samples were incubated in RPMI-1640 and following the experimental procedure shock frozen in liquid nitrogen and homogenized in a pre-chilled mortar before nuclear extracts were prepared (Supplemental Material A).

Ozonation of Reagents

Aqueous ozone was applied to the cells in form of ozonized medium without fetal calf serum ($O_3$-medium) or ozonized phosphate-buffered saline ($O_3$-phosphate-buffered saline) without/with 1 g/L amino acids or 2 g/L glucose. These solutions were treated with gaseous ozone (75 µg/mL, 15 min) using an ozone generator (Ozonosan-photonic, Dr. Hansler, Iffezheim, Germany). This condition, which applied to water would result in a final ozone concentration of 20 µg/mL (saturation point), was defined as the 100% ozonation state. For dose response experiments, the solutions were accordingly diluted. The ozone gas concentration was monitored by a photometer integrated in the ozone generator and confirmed by another ozone gas detector (GM-6000-NZL, Anseros, Tubingen, Germany). The ozone concentrations of the respective aqueous solutions were monitored photometrically (Palintest, Gateshead, England).

Electrophoretic Mobility Shift Assay

Nuclear extracts of cell lines or tissue debris were prepared and electrophoretic mobility shift assay was performed (Page et al., 1999; Supplemental Material A). The prototypic immunoglobulin κ-chain oligonucleotide was used as a probe and labeled with the Klenow fragment of DNA polymerase I (Roche, Penzberg, Germany) together with [$\alpha$-$^{32}$P]dCTP (PerkinElmer-LifeSciences, Brussels, Belgium). The Sp-1 consensus oligonucleotide (Promega) was labeled with [$\gamma$-$^{32}$P]ATP (PerkinElmer-LifeSciences) and T4-polynucleotide-kinase (Roche). Samples were run on non-denaturing 4% polyacrylamide gels and analyzed by autoradiography.

Western Blot Analysis

Cytosolic extracts were isolated and electrophoresis was performed (Page et al., 1999; Supplemental Material A). After transfer, the membranes were incubated with IκBα (Santa-Cruz-Biotechnology, Santa Cruz, USA) or actin antibodies (Sigma-Aldrich, Deisenhofen, Germany) followed by secondary peroxidase-conjugated antibodies (Dianova, Hamburg, Germany). Antibody binding was visualized on X-ray-film using Chemiluminescent-Reagent-Plus (PerkinElmer-LifeSciences).

Determination of Cytokines

Interleukin-8 and -1β concentrations in supernatants were measured by immunoassays (R&D-Systems, Wiesbaden, Germany; Bender-MedSystems, Vienna, Austria).

Luciferase Assay

For luciferase assays, HeLa cells were transiently transfected with a firefly-luciferase reporter plasmid (pGL2-3 KB-Luc, 3 KB binding motifs) together with a constitutively active Renilla-luciferase plasmid, pRLtk (Promega) (Page et al., 1999; Supplemental Material A), using a Superfect-based protocol (Qiagen, Hilden, Germany). Subsequent to stimulation, cells were lysed and luciferase-activity was determined with the Dual-Luciferase-Reporter-Assay (Promega). Results were expressed as relative luciferase-activity (firefly relative light-units divided by Renilla relative light-units).

RESULTS OF THE EXAMPLES

NF-κB Activation is Inhibited by $O_3$-Medium

First, oral epithelial cells (BHY), gingival fibroblasts (HGF-1) and HeLa epithelial cells were incubated in $O_3$-medium to investigate whether this is a condition which directly activates NF-κB. Dose response and time course experiments demonstrated that $O_3$-medium alone did not modulate the NF-κB-system (data not shown). Next, we tested if preincubation with $O_3$-medium affected the activation of NF-κB by other stimuli. Cells were preincubated with $O_3$-medium followed by exposure to TNF and optimal cellular conditions were again evaluated by dose response/time course experiments (data not shown). In the absence of ozone a marked activation of NF-κB by TNF was observed (FIGS. 1A,B). Incubation with $O_3$-medium, however, inhibited this activation, whereas constitutive Sp-1-binding was unchanged. A potential toxicity of $O_3$-medium was excluded by monitoring cell morphology, tryphan-blue-exclusion and ATP levels (Cell-Viability-Assay) (Supplemental Material B). As a positive control, preincubation with the proteasome inhibitor PSI (10 µM, 1 hr) markedly prevented TNF-induced NF-κB-activity (BHY, inhibition by 68±7%; HeLa, inhibition by 75±6%; n=3). Furthermore, we investigated whether $O_3$-medium also modulates NF-κB-activity in periodontal ligament tissue debris from the root surface of periodontal-diseased teeth. These experiments revealed a strong NF-κB-binding-activity when this tissue was incubated in medium alone, which was markedly inhibited following treatment with ozonized medium (FIG. 1C).

IκBA Proteolysis is Inhibited in the Presence of $O_3$-Medium

Figure 2:
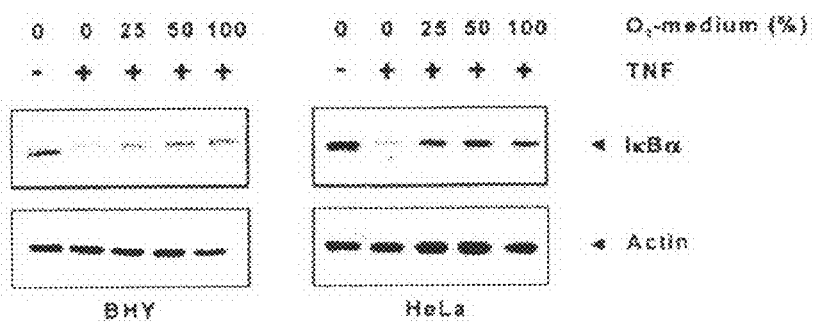
Figure 2:
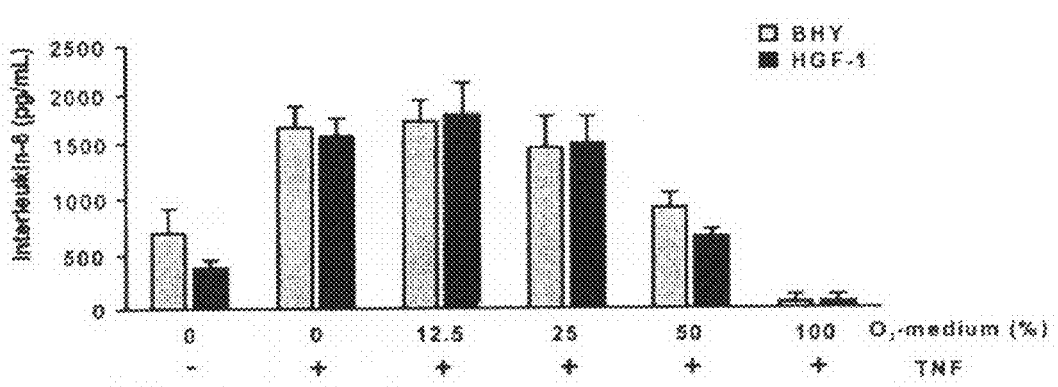
Figure 2:
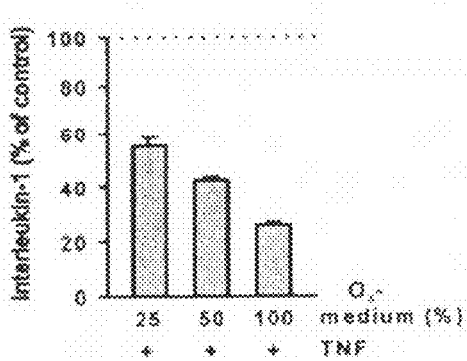
Figure 2:
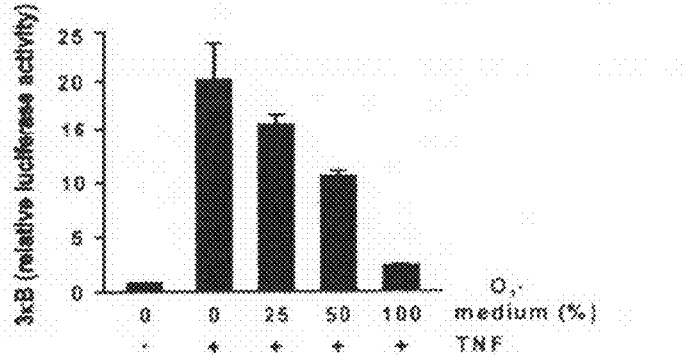

Next, we investigated if the level of the NF-κB inhibitor IκB (was affected by $O_3$-medium. Stimulation of cells with TNF led to a proteolysis of IκBα (FIG. 2A). However, in $O_3$-medium-preincubated cells, this TNF-induced IκBα degradation was inhibited, whereas constitutive actin levels were unchanged.

Target Gene Expression and κB-Dependent Transcription are Prevented

Functional consequences were studied by measuring cytokine levels in culture supernatants. Consistent with the results above, preincubation with $O_3$-medium led to a dose-dependent inhibition of TNF-induced production of interleukin-8 (FIG. 2B) and interleukin-1β (FIG. 2C). In addition, cells were transfected with a KB-dependent luciferase construct and treated as described before to monitor a direct impact on KB-dependent transcription. TNF induced a marked increase in transcriptional activity, which again was strongly inhibited by $O_3$-medium (FIG. 2D).

$O_3$-Amino Acids Selectively Inhibit NF-κB

Figure 3:
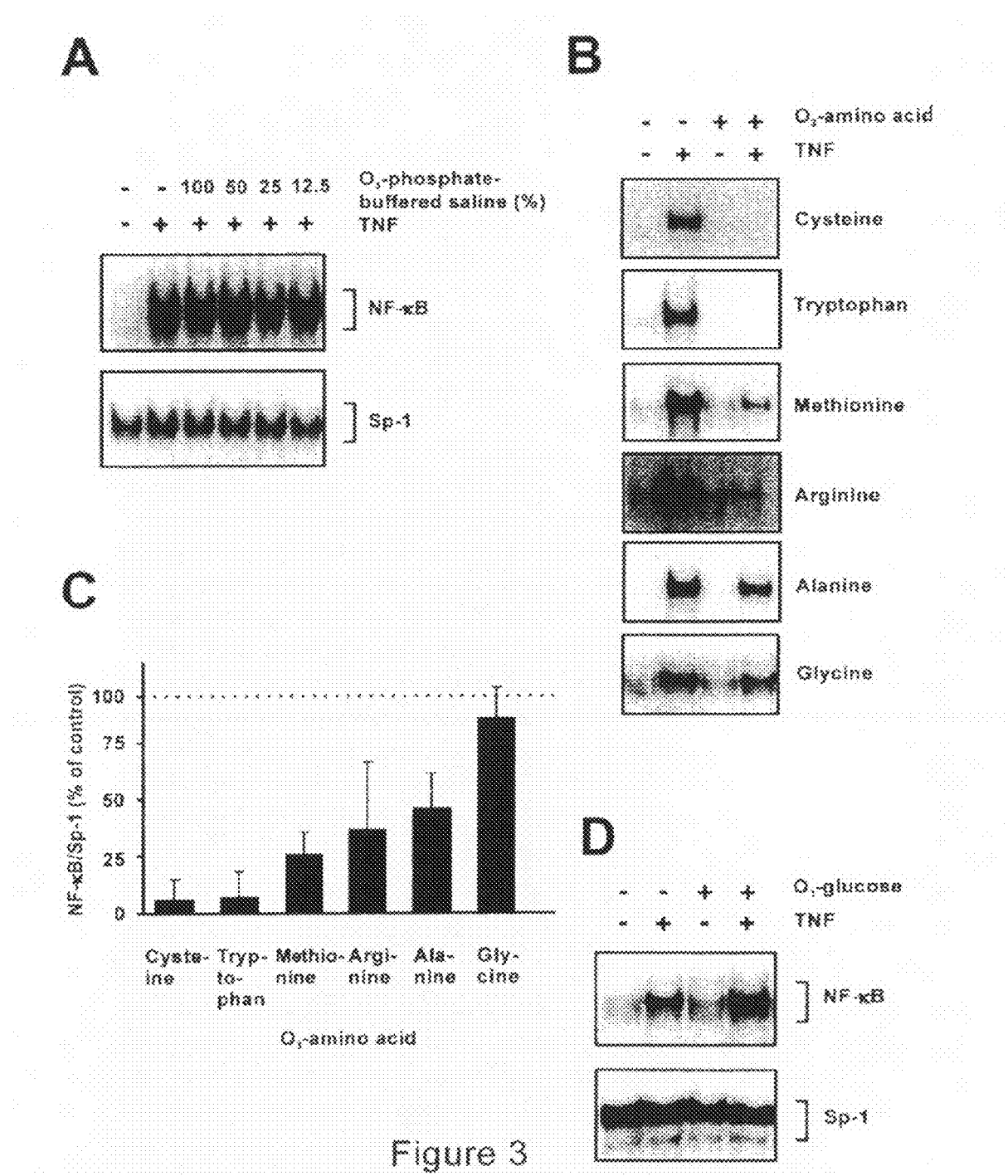
Figure 4:
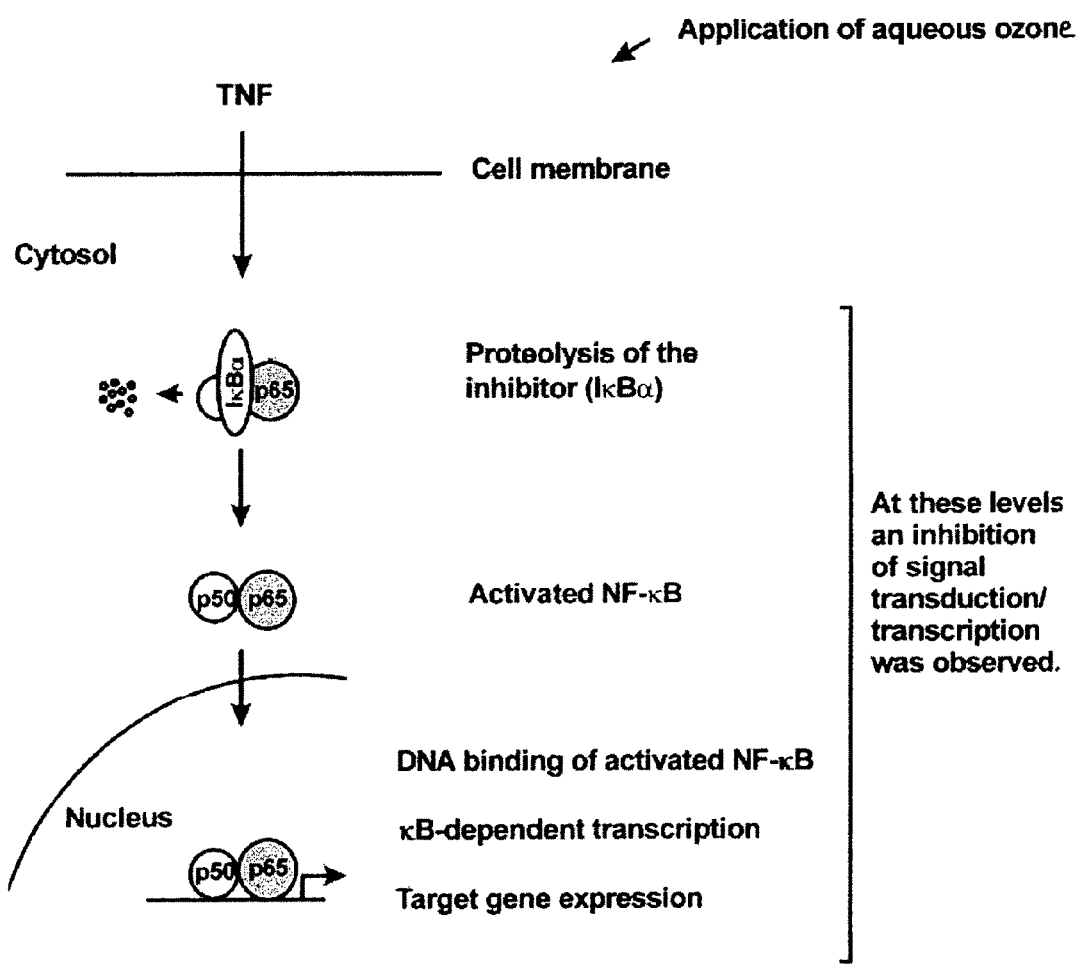

The inhibitory effect of $O_3$-medium could be due to ozone itself or ozonized medium constituents. Therefore, cells were preincubated with $O_3$-phosphate-buffered saline without further ingredients. In contrast to the results obtained above, the NF-κB-activation by TNF was not inhibited in all three cell lines by $O_3$-phosphate-buffered saline (FIG. 3A, data not shown). This indicates that the inhibitory effect of $O_3$-medium is not directly caused by ozone but rather mediated by the formation of medium ozonation-products. To identify these inhibitory ozonation-products, various amino acids (medium concentration) of the different groups (Cataldo, 2003), as major medium components, were added to phosphate-buffered saline prior to ozonation.

After preincubation of cells with ozonized and non-ozonized amino acids, TNF was added. Dependent on the different ozonized amino acids, NF-κB-activity was variously affected: the sulfhydryl-group-containing cysteine and the aromatic tryptophan blocked the NF-κB signal almost completely (FIGS. 3B,C); the sulfur-containing methionine resulted in a clear inhibition, the basic arginine in a modest and the nonpolar alanine in a slight reduction of NF-κB-activity, whereas the small, nonpolar glycine or non-ozonized amino acids did not have any effect. Similar, dose-dependent effects were observed in all three cell lines (data not shown).

To determine whether the inhibition of TNF-signaling by $O_3$-medium was also mediated by glucose, we added glucose (medium concentration) to phosphate-buffered saline followed by ozonation and treated the cells as described above. These experiments showed that the NF-κB-activity was not inhibited by $O_3$-glucose (FIG. 3D). Taken together, these results signify that ozonized amino acids, to a varying extent, are crucial in the therapeutical and prophylactic uses as described above.

SUMMARY AND INTERPRETATION OF THE EXPERIMENTAL DATA

Earlier reports using gaseous ozone throughout showed an activation of NF-κB (Haddad et al., 1996; Laskin et al., 2002). Contrary thereto and quite unexpected, an inhibitory activity of ozone under certain conditions on NF-κB has been shown by the present inventors.

First of all and quite surprisingly, TNF-signaling was unaffected when 03-phosphate-buffered saline was used instead of $O_3$-medium, which indicates that ozone itself is not able to inhibit NF-κB. Therefore, the question was which ozonation-product in the $O_3$-medium was responsible for this effect. To this end, the inventors added various amino acids from the different groups to phosphate-buffered saline (medium concentration) and found that TNF-induced NF-κB activation was differently affected. The ozonized sulfhydryl-group-containing cysteine as well as the aromatic tryptophan were found to be most effective in inhibiting NF-κB.

The consequences of the inhibitory effects of ozonized amino acids in aqueous solution on NF-κB found herein are of great medical importance. The attenuated activation of the host immune system may e.g. reduce the peridontitis-associated tissue destruction.

In summary, the present invention establishes a condition under which ozonized amino acids in aqueous solution and further also in non-aqueous solutions or as solid substance exert inhibitory effects on the NF-κB-system showing that it could have anti-inflammatory and immune-modulatory capacities and also antimicrobial capacity optionally in combination with ozone or any other antimicrobial agent. Thereby, the present data provide the experimental basis for an efficient use of a combination of aqueous ozone and amino acids and ozonized amino acids for the treatment of inflammatory diseases and microbial infections, particularly in the oral cavity.

REFERENCES

1. Arita M, Nagayoshi M, Fukuizumi T, Okinaga T, Masumi S, Morikawa M, Kakinoki Y, Nishihara T (2005). Microbicidal efficacy of ozonated water against *Candida albicans* adhering to acrylic denture plates. *Oral Microbiol Immunol* 20:206-210.
2. Bartold P M, Narayanan A S (2006). Molecular and cell biology of healthy and diseased periodontal tissues. *Periodontol 2000* 40:29-49.
3. Baysan A, Lynch E (2004). Effect of ozone on the oral microbiota and clinical severity of primary root caries. *Am J Dent* 17:56-60.
4. Bonizzi G, Karin M (2004). The two NF-κB activation pathways and their role in innate and adaptive immunity. *Trends Immunol* 25:280-288.
5. Cataldo F (2003). On the action of ozone on proteins. *Polym Degrad Stab* 82:105-114.
6. Chen G, Goeddel D V (2002). TNF-R1 signaling: a beautiful pathway. *Science* 296:1634-1635.
7. Ebensberger U, Pohl Y, Filippi A (2002). PONA-expression of cementoblasts and fibroblasts on the root surface after extraoral rinsing for decontamination. *Dent Traumatol* 18:262-266.
8. Filippi A (2001). The effects of ozonized water on epithelial wound healing. *Dtsch Zahnärztl Z* 56:104-108.
9. Gamonal J, Acevedo A, Bascones A, Jorge O, Silva A (2000). Levels of interleukin-1 beta, -8, and -10 and RANTES in gingival crevicular fluid and cell populations in adult periodontitis patients and the effect of periodontal treatment. *J Periodontol* 71:1535-1545.
10. Graves D T, Jiang Y, Genco C (2000). Periodontal disease: bacterial virulence factors, host response and impact on systemic health. *Curr Opin Infect Dis* 13:227-232.
11. Haddad E B, Salmon M, Koto H, Barnes P J, Adcock I, Chung K F (1996). Ozone induction of cytokine-induced neutrophil chemoattractant (CINC) and nuclear factor-Kb in rat lung: inhibition by corticosteroids. *FEBS Lett* 379:265-268.
12. Honda T, Domon H, Okui T, Kajita K, Amanuma R, Yamazaki K (2006). Balance of inflammatory response in stable gingivitis and progressive periodontitis lesions. *Clin Exp Immunol* 144:35-40.
13. Huth K C, Jakob F M, Saugel B, Cappello C, Paschos E, Hollweck R, Hickel R, Brand K (2006). Effect of ozone on oral cells compared to established antimicrobials. *Eur J Oral Sci* 14:435-440.
14. Laskin D L, Fakhrzadeh L, Heck D E, Gerecke D, Laskin J D (2002). Upregulation of phosphoinositide 3-kinase and protein kinase B in alveolar macrophages following ozone inhalation. Role of NF-κB and STAT-1 in ozone-induced nitric oxide production and toxicity. *Mol Cell Biochem* 234-235:91-98.
15. Lin C P, Chen Y J, Lee Y L, Wang J S, Chang M C, Lan W H, Chang H H, Chao W M W, Tai T F, Lee M Y, Lin B R, Jeng J H (2004). Effects of root-end filling materials and eugenol on mitochondrial dehydrogenase activity and cytotoxicity to human periodontal ligament fibroblasts. *J Biomed Mater Res B Appl Biomater* 71B:429-440.
16. Madianos P N, Bobetsis Y A, Kinane D F (2005). Generation of inflammatory stimuli: how bacteria set up inflammatory responses in the gingiva. *J Clin Periodontol* 32 (Suppl 6):57-71.
17. Márton I J, Kiss C (2000). Protective and destructive immune reactions in apical periodontitis. *Oral Microbiol Immunol* 15:139-150.
18. Nagayoshi M, Fukuizumi T, Kitamura C, Yano J, Terashita M, Nishihara T (2004a). Efficacy of ozone on survival and permeability of oral microorganisms. *Oral Microbiol Immunol* 19:240-246.

19. Nagayoshi M, Kitamura C, Fukuizumi T, Nishihara T, Terashita M (2004b). Antimicrobial effect of ozonated water on bacteria invading dentinal tubules. *J Endod* 30:778-781.
20. Nair P N (2004). Pathogenesis of apical periodontitis and the causes of endodontic failures. *Crit Rev Oral Biol Med* 15:348-381.
21. Nichols T C, Fischer T H, Deliargyris E N, Baldwin A S Jr (2001). Role of nuclear factor-kappa B (NF-kappa B) in inflammation, periodontitis, and atherogenesis. *Ann Periodontol* 6:20-29.
22. Page S, Fischer C, Baumgartner B, Haas M, Kreusel U, Loidl G, Hayn M, Ziegler-Heitbrock HWL, Neumeier D, Brand K (1999). 4-Hydroxynonenal prevents NF-κB activation and tumor necrosis factor expression by inhibiting IκB phosphorylation and subsequent proteolysis. *J Biol Chem* 274:11611-11618.
23. Paraskeva P, Graham N J D (2002). Ozonation of municipal wastewater effluents. *Water Environ Res* 74:569-581.
24. Restaino L, Frampton E W, Hemphill J B, Palnikar P (1995). Efficacy of ozonated water against various food-related microorganisms. *Appl Environ Microbiol* 61:3471-3475.
25. Sabeti M, Simon J, Kermani V, Valles Y, Rostein I (2005). Detection of receptor activator of NF-κβ ligand in apical periodontitis. *J Endod* 31:17-18.

The invention claimed is:

1. A method of treating an inflammation in a human or animal patient comprising the step of administering a pharmaceutical preparation to a patient in need thereof in a therapeutically effective amount in order to ameliorate or remove the inflammation, wherein the pharmaceutical preparation comprises:
   ozone and at least one monomeric amino acid having one or more oxidation-sensitive side chains, or
   at least one ozonized monomeric amino acid.
2. The method of claim 1, wherein the NF-κB-system is inhibited.
3. The method according to claim 1, wherein the amino acid is selected from the group consisting of sulfur containing amino acids, aromatic amino acids, and/or amino acids having at least one unsaturated functional group.
4. The method of claim 3, wherein the preparation comprises one or more of the amino acids cysteine, methionine, tryptophan, tyrosine, phenylalanine, histidine, and arginine.
5. The method according to claim 1, wherein the amino acid or ozonized amino acid is present in an amount of 0.01-100 g/l and wherein the ozone is present in an amount of 0.01-20 µg/ml.
6. The method according to claim 1, wherein at least one further pharmaceutically active substance is included in the preparation, which substance has anti-inflammatory activities and/or anti-microbial activities and/or immune-modulating activities.
7. The method of claim 6, wherein the at least one further pharmaceutically active substance is a substance active in the oral, dental, or throat region.
8. The method according to claim 6, wherein additionally pharmaceutically acceptable auxiliary substances are included.
9. The method according to claim 1, wherein said ozone and at least one amino acid are present in aqueous solution, and wherein said at least one ozonized amino acid is present in aqueous or non-aqueous solution or in dry form.
10. The method of claim 1, wherein the preparation is administered to the oral, dental or throat region.
11. The method of claim 1, wherein the preparation is administered in a single dosage volume of 5-10 ml and the treatment is performed for about 1 min.
12. The method of claim 1, wherein the preparation is administered in order to rinse one or more periodontal pocket(s).
13. The method of claim 1, wherein the treatment is for dermal and mucosal inflammatory diseases, viral, bacterial or fungal caused diseases, wound-healing disturbances or ulcera.
14. The method of claim 1, which is for treating oral inflammations.
15. The method of claim 14, wherein the oral inflammations are selected from the group consisting of periodontal disease and apical periodontitis.
16. The method of claim 14, wherein the oral inflammations are endodontic root canals, gingivitis, impaired wound healing, after surgical interventions, periimplantitis, or caries.
17. The method of claim 16, wherein the preparation is a gingivitis preventative or treating mouthrinse.

* * * * *